US008277836B2

(12) United States Patent
Sawatzki et al.

(10) Patent No.: US 8,277,836 B2
(45) Date of Patent: *Oct. 2, 2012

(54) CARBOHYDRATES MIXTURE

(75) Inventors: Gunther Sawatzki, Munzenberg (DE); Bernd Stahl, Friedrichsdorf (DE)

(73) Assignee: N.V. Nutricia, Zoetermeer (NL)

(*) Notice: Subject to any disclaimer, the term of this patent is extended or adjusted under 35 U.S.C. 154(b) by 237 days.

This patent is subject to a terminal disclaimer.

(21) Appl. No.: 12/565,512

(22) Filed: Sep. 23, 2009

(65) Prior Publication Data

US 2010/0016214 A1    Jan. 21, 2010

Related U.S. Application Data

(63) Continuation of application No. 11/649,879, filed on Jan. 5, 2007, now Pat. No. 7,601,364, which is a continuation of application No. 09/774,188, filed as application No. PCT/EP99/05878 on Aug. 11, 1999, now abandoned.

(30) Foreign Application Priority Data

Aug. 11, 1998  (DE) ................................. 198 36 399

(51) Int. Cl.
*A61K 47/00*   (2006.01)
(52) U.S. Cl. ............... 424/439; 514/23; 514/53; 514/54
(58) Field of Classification Search .................... 424/439
See application file for complete search history.

(56) References Cited

U.S. PATENT DOCUMENTS

| | | | |
|---|---|---|---|
| 2,981,629 A | 4/1961 | Ginnette et al. |
| 3,956,228 A | 5/1976 | Nogami |
| 4,237,118 A | 12/1980 | Howard |
| 4,412,946 A | 11/1983 | Zalisz et al. |
| 4,438,147 A | 3/1984 | Hedrick, Jr. |
| 5,292,723 A | 3/1994 | Audry et al. |
| 5,374,657 A | 12/1994 | Kyle |
| 5,444,054 A | 8/1995 | Garleb et al. |
| 5,472,952 A | 12/1995 | Smidt et al. |
| 5,502,041 A | 3/1996 | Moen et al. |
| 5,531,988 A | 7/1996 | Paul |
| 5,629,023 A | 5/1997 | Bland |
| 5,629,040 A | 5/1997 | Takemori et al. |
| 5,709,888 A | 1/1998 | Gil et al. |
| 5,733,579 A | 3/1998 | Wolf et al. |
| 5,744,134 A | 4/1998 | Paul |
| 5,773,094 A | 6/1998 | Kruckel |
| 5,776,887 A | 7/1998 | Wibert et al. |
| 5,792,754 A | 8/1998 | Green et al. |
| 5,827,526 A | 10/1998 | Dohnalek et al. |
| 5,840,361 A | 11/1998 | Theuer et al. |
| 5,846,569 A | 12/1998 | Anderson et al. |
| 5,882,648 A | 3/1999 | Yoshihara et al. |
| 6,051,260 A | 4/2000 | Liska et al. |
| 6,197,758 B1 | 3/2001 | Ohtsuki et al. |
| 6,231,889 B1 | 5/2001 | Richardson et al. |
| 6,306,908 B1 | 10/2001 | Carlson et al. |
| 6,337,137 B1 | 1/2002 | Koldijk et al. |
| 6,426,110 B1 | 7/2002 | Basa |
| 6,451,584 B2 | 9/2002 | Tomita et al. |
| 6,468,987 B1 | 10/2002 | Demichele et al. |
| 6,576,251 B1 * | 6/2003 | Stahl et al. ..................... 424/439 |
| 6,632,445 B2 | 10/2003 | Richardson et al. |
| 6,645,543 B2 | 11/2003 | Gohman et al. |
| 6,713,113 B2 | 3/2004 | Bisperink et al. |
| 6,737,089 B2 | 5/2004 | Wadsworth et al. |
| 6,794,495 B1 | 9/2004 | Sorensen |
| 6,846,501 B2 | 1/2005 | Prosise et al. |
| 6,872,416 B2 | 3/2005 | Chmiel et al. |
| 6,974,841 B1 | 12/2005 | Rapisarda |
| 7,351,715 B2 | 4/2008 | Richardson et al. |
| 7,576,070 B2 | 8/2009 | Kunz et al. |
| 7,601,364 B2 | 10/2009 | Sawatzki et al. |
| 2002/0016289 A1 | 2/2002 | Conneely et al. |

(Continued)

FOREIGN PATENT DOCUMENTS

AU      1997/28718      7/1997

(Continued)

OTHER PUBLICATIONS

Reddy et al (Effect of dietary oligofructose and inulin on colonic preneoplastic aberrant crypt foci inhibition. Carcinogenesis 18 (7): 1371-1374 (1997).*
Crittenden et al (Production, properties and applications of food-grade oligosaccharides. Trends in Food Science & Technologies, vol. 7, Nov. 1996. pp. 353-361).*
Alter et al., "Sequential deregulation of NK cell subset distribution and function starting in acute HIV-1 infection," *Blood*, vol. 106, No. 10, Nov. 15, 2005, pp. 3366-3369.
Anonymous, "Larch Arabinogalactan," *Alternative Medicine Review*, vol. 5, No. 5, 2000, pp. 463-466.
Database CA 'Online! Chemical Abstracts Service, Columbus, Oh, Nogami, "Resin Compositions for low-temperature curable powder paints," retrieved from STN Database accession No. 87:137415 abstract & JP 53 042340 B, Nov. 10, 1978.

(Continued)

*Primary Examiner* — Jake M. Vu
(74) *Attorney, Agent, or Firm* — Gilberto M. Villacorta; Sunit Talapatra; Foley & Lardner LLP

(57) ABSTRACT

A carbohydrate mixture for dietetic foods and pharmaceuticals is provided. The carbohydrate mixture comprises two different, substantially soluble carbohydrate components A and B, which remain undigested in the gastrointestinal tract and enter the large intestine without being resorbed. Carbohydrate component A may comprise at least one monosaccharide or of at least one oligosaccharide (disaccharide to hexasaccharide) or a mixture of two or more of these saccharides. Carbohydrate component B may comprise a polysaccharide (from heptasaccharide onwards) or a mixture of two or more polysaccharides. Carbohydrate component A=5 to 95 wt-% and carbohydrate component B=5 to 95 wt-% of the sum of the carbohydrate components A+B (=100 wt-%), and at least 80 wt-% of the carbohydrates/saccharides of both carbohydrate components have a prebiotic effect. The carbohydrate mixtures have not only a nutritive effect but they also stimulate health-promoting microorganisms present in the natural flora of the large intestine.

16 Claims, No Drawings

U.S. PATENT DOCUMENTS

| | | | |
|---|---|---|---|
| 2002/0044988 A1 | 4/2002 | Fuchs et al. |
| 2003/0022863 A1 | 1/2003 | Stahl et al. |
| 2003/0165604 A1 | 9/2003 | Tsubaki et al. |
| 2004/0072791 A1 | 4/2004 | Kunz et al. |
| 2004/0122105 A1 | 6/2004 | Bettle et al. |
| 2004/0219188 A1 | 11/2004 | Comer et al. |
| 2006/0110516 A1 | 5/2006 | Holtus |
| 2007/0036839 A1 | 2/2007 | Tuduri et al. |
| 2007/0166446 A1 | 7/2007 | Boursier |
| 2008/0015166 A1 | 1/2008 | Van Tol |
| 2008/0064656 A1 | 3/2008 | Van Tol |
| 2008/0138435 A1 | 6/2008 | Van Den Berg et al. |
| 2008/0171720 A1 | 7/2008 | Garssen et al. |
| 2008/0207559 A1 | 8/2008 | Sawatzki et al. |
| 2009/0082249 A1 | 3/2009 | Garssen et al. |
| 2010/0069320 A1 | 3/2010 | Speelmans |
| 2010/0167982 A1 | 7/2010 | Van Tol et al. |
| 2011/0077189 A1 | 3/2011 | Vriesema |
| 2011/0236500 A1 | 9/2011 | Van Den Berg et al. |

FOREIGN PATENT DOCUMENTS

| | | |
|---|---|---|
| CA | 2340103 | 2/2000 |
| DE | 28 44 861 A1 | 4/1980 |
| DE | 37 34962 C1 | 1/1989 |
| DE | 199 40 011 A1 | 3/2001 |
| DE | 100 27 050 A1 | 12/2001 |
| DE | 101 36 260 A1 | 2/2003 |
| EP | 0 355 905 A1 | 2/1990 |
| EP | 0 378 824 B1 | 7/1990 |
| EP | 0382355 | 8/1990 |
| EP | 0 484 266 A2 | 5/1992 |
| EP | 0504055 A | 9/1992 |
| EP | 0511761 A1 | 11/1992 |
| EP | 0307523 B1 | 3/1993 |
| EP | 0593774 | 4/1994 |
| EP | 0 596 717 A1 | 5/1994 |
| EP | 0 615 752 A1 | 9/1994 |
| EP | 0 641 562 A1 | 3/1995 |
| EP | 0692252 A1 | 1/1996 |
| EP | 0705539 A2 | 4/1996 |
| EP | 0 711 503 A2 | 5/1996 |
| EP | 0756828 A | 2/1997 |
| EP | 0 813 815 A1 | 12/1997 |
| EP | 0 745 330 B1 | 10/1998 |
| EP | 0 745 001 B1 | 11/1998 |
| EP | 0958825 A1 | 11/1999 |
| EP | 1 074 181 A1 | 2/2001 |
| EP | 0 631 731 B1 | 9/2001 |
| EP | 1 155 627 A1 | 11/2001 |
| EP | 1 105 002 B1 | 7/2002 |
| EP | 1 228 694 A1 | 8/2002 |
| EP | 0 941 088 B1 | 3/2003 |
| EP | 1 321 527 | 6/2003 |
| EP | 1 597 978 A1 | 11/2005 |
| EP | 1 454 990 B1 | 2/2006 |
| EP | 1 721 611 A1 | 11/2006 |
| EP | 1 723 951 A1 | 11/2006 |
| EP | 1 672 987 B1 | 5/2007 |
| EP | 1 815 755 B1 | 4/2009 |
| FR | 2 781 673 A1 | 2/2000 |
| FR | 2 866 203 A1 | 8/2005 |
| GB | 1305071 | 1/1973 |
| JP | 53-42340 | 11/1978 |
| JP | 2-286058 A | 11/1990 |
| JP | 08-151328 A | 6/1996 |
| JP | 9-065855 A | 3/1997 |
| JP | 10-175867 A | 6/1998 |
| JP | 2003 146887 | 5/2003 |
| NL | 1018832 | 3/2003 |
| WO | WO 92/22588 A1 | 12/1992 |
| WO | WO 95/26646 | 10/1995 |
| WO | WO 96/13271 A | 5/1996 |
| WO | WO 97/02829 | 1/1997 |
| WO | WO 97/34615 | 9/1997 |
| WO | WO-98/06276 A1 | 2/1998 |
| WO | WO 98/11910 A1 | 3/1998 |
| WO | WO 98/15196 A1 | 4/1998 |
| WO | WO 98/26787 | 6/1998 |
| WO | WO 98/31241 * | 7/1998 |
| WO | WO 98/31241 A1 | 7/1998 |
| WO | WO-98/46764 A1 | 10/1998 |
| WO | WO 99/53777 A1 | 10/1999 |
| WO | WO 01/41581 A1 | 6/2001 |
| WO | WO 01/60378 A2 | 8/2001 |
| WO | WO 01/78530 A2 | 10/2001 |
| WO | WO 02/42484 A2 | 5/2002 |
| WO | WO 02/47612 | 6/2002 |
| WO | WO 02/060283 A2 | 8/2002 |
| WO | WO 02/076471 A1 | 10/2002 |
| WO | WO 03/093322 A2 | 11/2003 |
| WO | WO-03/102205 A1 | 12/2003 |
| WO | WO 04/000042 A2 | 12/2003 |
| WO | WO 04/000340 A2 | 12/2003 |
| WO | WO 2004/019699 A1 | 3/2004 |
| WO | WO 2004/026294 A1 | 4/2004 |
| WO | WO 2004/052121 A1 | 6/2004 |
| WO | WO 2004/112508 A1 | 12/2004 |
| WO | WO 2004/112509 A2 | 12/2004 |
| WO | WO 2004/113415 A1 | 12/2004 |
| WO | WO 2005/039319 A1 | 5/2005 |
| WO | WO 2005/039597 A2 | 5/2005 |
| WO | WO 2005/067955 | 7/2005 |
| WO | WO 2005/110121 A1 | 11/2005 |
| WO | WO 2005/122790 A1 | 12/2005 |
| WO | WO 2006/007676 A1 | 1/2006 |
| WO | WO-2006/014519 A1 | 2/2006 |
| WO | WO 2006/112694 A2 | 10/2006 |
| WO | WO 2006/112716 A2 | 10/2006 |
| WO | WO 2006/112717 A2 | 10/2006 |
| WO | WO 2007/016132 A2 | 2/2007 |
| WO | WO 2007/115210 | 10/2007 |
| WO | WO 2009/096772 A1 | 8/2009 |
| WO | WO 2009/096789 A1 | 8/2009 |

OTHER PUBLICATIONS

Database Medline [Online], US NLM, Dec. 1994, Malorni et al.: "Thiol supplier N-acetylcysteine enhances conjugate formation between natural killer cells and K562 or U937 targets but increases the lytic function only against the latter,", Database accession No. NLM7721335, & Immunology Letters, vol. 43, No. 3, Dec. 1994, 1 page [XP002474080].

Database WPI, Week 200634, Derwent Publications Ltd., London, GB, AN 2006-323978 & JP 2006 115826 A, May 2006 [XP-002474081].

Facchini et al., "Increased number of circulating Leu 11+ (CD 16) large granular lymphocytes and decreased NK activity during human ageing," Clinical Experimental Immunology, vol. 68, No. 2, 1987, pp. 340-347.

Ferrandez et al.: "Effects in vitro of several antioxidants on the natural killer function of aging mice—differing rolesfor IFN-gamma and IL-2," Experimental Gerontology, vol. 34, No. 5, Aug. 1999, pp. 675-685 [XP002474079].

Ghoneum et al., "Production of Tumor Necrosis Factor-Alpha and Interferon-Y from Human Peripheral Blood Lymphocytes by MGN-3, a Modified Arabinoxylan from Rice Bran, and Its Synergy with Interleukin-2 In Vitro," Cancer Detection and Prevention, vol. 24, No. 4, 2000, pp. 314-324.

Ghoneum et al., "Enhancement of Natural Killer Cell Activity of Aged Mice by Modified Arabinoxylan Rice Bran (MGN-3/Biobran)," J. Pharm. and Pharmacology, vol. 56, No. 12, Dec. 2004, pp. 1581-1588.

Hauer et al., "Mechanism of Stimulation of Human Natural Killer Cytotoxicity by Arabinogalactan from Laris Occidentalis," Cancer Immuno. Immunotherapy, vol. 36, No. 4, 1993, pp. 237-244.

Jenkins et al., "Inulin, Oligofructose and Intestinal Function," J. Nutrition, vol. 129, 1999, pp. 1431S-1433S.

Marini et al., "Pro- and pre-biotics administration in preterm infants: colonization and influence on faecal flora," Acta Paediatr. Suppl., vol. 441, 2003, pp. 80-81.

Sansoni, "Lymphocyte Subsets and Natural Killer Cell Activity in Healthy Old People and Centenarians," Blood, vol. 82, No. 9, Nov. 1, 1993, pp. 2767-2773.

Usami et al, "Effect of eicosapentaenoic acid (EPA) on tight junction permeability in intestinal monolayer cells," *Clinical Nutrition*, vol. 20, No. 4, 2001, pp. 351-359.

Watzl et al., "Inulin, oligofructose and immunomodulation," *British Journal of Nutrition*, vol. 93, No. 1, 2005, pp. S49-S55 [XP002474088].

Notice of Allowance and Fee(s) Due corresponding to U.S. Appl. No. 11/649,879, dated Aug. 3, 2009, 7 pages.

14.0 Spray Drying, obtained from http://class.fst.ohio-state.edu/Dairy_Tech/14Spraydrying.htm, Mar. 1, 2000, 15 pages.

AIDS Fact Sheet: T-cell tests; also available at http://web.archive.org/web/20040217112225/http://www.aids.org/factSheets/124-T-Cell-Tests.html, published 2004; last viewed Oct. 21, 2009.

Alanate 385 Dispersible Calcium Caseinate, specification sheet, 2 pages, no date available (US 2006-0110516, Office Action dated Mar. 1, 2010).

Boehm et al., "Supplementation of a bovine milk formula with an oligosaccharide mixture increases counts of faecal bifidobacteria in preterm infants," *Fetal & Neonatal*, vol. 86, No. 3, May 2002, pp. F178-F181.

Boehm, "Prebiotic concept for infant nutrition," *Acta Paediatrica Suppl.*, vol. 441, 2003, pp. 64-67.

Boehm et al., "Prebiotics and Immune Responses," *Journal of Pediatric Gastroenterology and Nutrition*, vol. 39, Jun. 2004, pp. S772-S773.

Boersma et al., "Vitamin E, lipid fractions, and fatty acid composition of colostrum, transitional milk, and mature milk: an international comparative study," *American Journal of Clinical Nutrition*, Dep. of Obstetrics & Gynaecology, State Univ. Groningen, EZ Groningen 9713, Netherlands, vol. 3, No. 5, 1991, p. 1197.

Breitkreutz et al., "Improvement of immune functions in HIV infection by sulfur supplementation: Two randomized trials," *Journal of Molecular Medicine* (Berlin), vol. 78, No. 1, 2000, pp. 55-62.

Buckler, "Prebiotics in infant nutrition," Internet article online Jul. 8, 2001, pp. 1-5 (XP002292254), retrieved from the Internet: URL:http://ww.se-neonatal.es/se-neonatal/oviedo2001/prebiotics.pdf on Aug. 11, 2004.

*CODEX Stan 72*, "Standard for Infant Formula and Formulas for Special Medical Purposes Intended for Infants," 1981, pp. 1-21.

Dairy Chemistry and Physics, University of Guelph, obtained from http://www.foodsci.uoguelph.ca/dairyedu/chem.html, Feb. 4, 2001, 16 pages.

Database CA 'Online! Chemical Abtracts Service, Columbus, Oh, Nogami, "Resin Compositions for low-temperature curable powder paints," retrieved from STN Database accession No. 87:137415 abstract & JP 53 042340 B, Nov. 10, 1078.

Database WPI, Section Ch. Week 198929, Derwent Publications Ltd., London, GB, AN 1989-211474.

Database WPI, Section Ch. Week 199615, Derwent Publications Ltd., London, GB, AN 1996-145913.

Database WPI Week 199633, Derwent Publications, Ltd., London, GB: AN 1996-329426 [XP 002426042].

Database WPI, Section Ch, Week 200261, Derwent Publications Ltd., London, GB, AN 2002-567199 & CN 1 343 727 A, Apr. 10, 2002 [XP 002344565].

Dongowski et al., "The Degree of Methylation Influences the Degradation of Pectin in the Intestinal Tract of Rats In Vitro," *The Journal of Nutrition*, vol. 132, 2002, pp. 1935-1944.

Droege, "Cysteine and glutathione deficiency in AIDS patients: A rationale for the treatment with N-acetylcysteine," *Pharmacology* (Basel), vol. 46, No. 2, 1993, pp. 61-65.

Droege et al, "Is AIDS the consequence of a virus-induced cysteine and glutathione deficiency? Chances and limitations of the treatment with N-acetyl-cysteine (NAC)," *AIDS Research and Human Retroviruses*, vol. 10, No. Suppl. 3, 1994, p. S65 (XP008052583).

Droege et al., "Role of cysteine and glutathione in HIV infection and other diseases associated with muscle wasting and immunological dysfunction," *FASEB Journal*, vol. 11, No. 13, Nov. 1997, pp. 1077-1089.

Droege et al., "Glutathione and immune fuction," *Proceedings of the Nutrition Society*, vol. 59, No. 4, Nov. 2000, pp. 595-600.

Elfstrand et al., "Immunoglobulins, growth factors and growth hormone in bovine colostrum and the effects of processing," *International Dairy Journal*, vol. 12, 2002, pp. 879-887.

Fanaro et al., "Galacto-oligosaccharides and long-chain fructo-oligosaccharides as prebiotics in infant formulas: A review," *Acta Paediatrica Suppl.*, 449, (2005), pp. 22-26, vol. 94.

Fidler et al., "Polyunsaturated fatty acid composition of human colostrum lipids in Slovenia: regional differences," *Food Technology and Biotechnology*, vol. 38, No. 2, 2000, pp. 149-153, Biotech. Fac., Inst. of Nutr., Univ. of Ljubljana, SI-1230 Domzale, Slovenia.

Fidler et al., "The fatty acid composition of human colostrum," *European Journal of Nutrition*, vol. 39, No. 1, Feb. 2000, pp. 31-37.

Glade, "Nutrition, Nutritional Pharmaceuticals," *Conference Summary: First Symposium of the Intentional College of Advanced Longevity Medicine*, Reno, Nevada, Oct. 11-13, 1998, vol. 16, issue 9, 2000, pp. 789-790.

Gonzalez et al., "Polysaccharides as Antiviral Agents: Antiviral Activity of Carrageenan," *Antimicrobial Agents and Chemotherapy*, vol. 31, No. 9, Sep. 1987, pp. 1388-1393, American Society for Microbiology, Washington, DC, US.

Harmsen et al., "Analysis of Intestinal Flora Development in Breast-Fed and Formula-Fed Infants by Using Molecular Identification and Detection Methods," *J. Pediatr. Gastroenterol. Nutr.*, vol. 30, 2000, pp. 61-67.

Hirayama, "Novel physiological functions of oligosaccharides," *Pure Appl. Chem.*, vol. 74, No. 7, 2002, pp. 1271-1279.

Hopkins et al., "Nondigestible Oligosaccharides Enhance Bacterial Colonization Resistance against Clostridium difficile In Vitro," *Applied and Environmental Microbiology*, vol. 69, No. 4, Apr. 2003, pp. 1920-1927.

International Search Report dated Feb. 29, 2000, PCT/EP1999/005878, 3 pages.

Isolauri et al., "Probiotics in the management of atopic eczema," *Clinical and Experimental Allergy*, vol. 30, 2000, pp. 1604-1610.

Jacobson et al., "Absolute or total lymphocyte count as a marker for the CD4 T lymphocyte criterion for initiating antiretroviral therapy," *AIDS* (Hagerstown), vol. 17, No. 6, Apr. 11, 2003, pp. 917-919 (XP008052430).

Klose et al., Chapter 7 entitled "Gums" in *CRC Handbook of Food Additives*, $2^{nd}$ ed, edited by Furia, 1972, pp. 305-307.

Kulkarni et al., "Immunostimulant activity of inulin isolated from *Saussurea lappa* roots," *Indian Journal of Pharmaceutical Sciences*, vol. 63, No. 4, Jul. 2001, pp. 292-294.

Laidlaw et al., "Effects of supplementation with fish oil-derived n-3 fatty acids and γ-linolenic acid on circulating plasma lipids and fatty acid profiles in women," *Am J Clin Nutr*, vol. 77, 2003, pp. 37-42.

Marshall, "Therapeutic Applications of Whey Protein," *Alternative Medicine Review*, vol. 9, No. 2, 2004, pp. 136-156.

Mata et al., "Evaluation of a recombinant Listeria monocytogenes expressing an HIV protein that protects mice against viral challenge," *Vaccine*, vol. 19, 2001, pp. 1435-1445.

MayoClinic.com "prevention of HIV/AIDS," also available at http://www/mayoclinic.com/health/hiv-aids/DS00005/DSECTION=prevention, last viewed Aug. 21, 2009.

McGraw-Hill's Access Science Encyclopedia of Science & Technology Online "Acid and Base," also available at http://www.accessscience.com/content.aspx?searchStr=acid&id=004400, last viewed Aug. 20, 2009.

McGraw-Hill's Access Science Encyclopedia of Science & Technology Online "oligosaccharide," also available at http://www.accessscience.com/content.aspx?searchStr=oligosaccharide&id=468300, last viewed Aug. 21, 2009.

*Merck Manual*, "Atopic and Alllergic Disorders," also available at http://www.merck.com/mmpe/sec13/ch165/ch165c.html?qt=allergy&alt=sh#sec13-ch165-ch165c-319, last viewed Mar. 16, 2010.

Miniello et al., "Prebiotics in infant milk formulas: New Perspectives," *Acta Paediatrica Suppl.*, 441, 2003, pp. 68-76.

Mori et al., "Effects of Glycyrrhizin (SNMC: Stronger Neo-Minophagen C) in hemophilia patients with HIV-1 Infection," *Tohoku J. Exp. Med.*, vol. 162, No. 2, 1990, pp. 183-193.

Moro et al., "Dosage-Related Bifidogenic Effects of Galacto- and Fructooligosaccharides in Formula-Fed Term Infants," *Journal of*

*Pediatric Gastroenterology and Nutrition*, vol. 34, No. 3, Mar. 2002, pp. 291-295, Raven Press, NY, NY.

Moro et al., "Effects of a new mixture prebiotics on faecal flora and stools in term infants," *Acta Paediatrica Suppl.*, vol. 91, No. 441, Sep. 2003, pp. 77-79.

Moro et al., "Reproducing the bifidogenic effect of human milk in formula-fed infants: Why and how?" *Acta Paediatrica Suppl.*, 449, vol. 94, 2005, pp. 14-17.

Murphy, "Non-polyol low-digestible carbohydrates: food applications and functional benefits," *British Journal of Nutrition*, vol. 85, suppl. 1, 2001, pp. S47-S53.

Nakano et al., "Anti-Human Immunodeficiency Virus Activity of Oligosaccharides from Rooibos Tea (*Aspalathus linearis*) Extracts in Vitro," *Leukemia*, vol. 11, No. suppl. 3, Macmillan Press Ltd., US, 1997, pp. 128-130.

Orafti, "inulin," also available at http://www.orafti.com/Our-Products/Inulin, last viewed Mar. 15, 2010.

Parcell, "Sulfur in Human Nutrition and Applications in Medicine," *Alternative Medicine Review*, vol. 7, No. 1, Feb. 2002, pp. 22-24, Thorne Research Inc., Sandpoint, US.

Patent Abstracts of Japan, vol. 013, No. 408 (C-634), Sep. 8, 1989 (JP 01 149730 A, Jun. 12, 1989).

Patent Abstracts of Japan, vol. 017, No. 119 (C-1034), Mar 12, 1993 (JP 04 300888 A, Oct. 23, 1992).

Reich et al, "Tonicity, Osmoticity, Osmolality, and Osmolarity," in Remington: *The Science and Practice of Pharmacy*, 20$^{th}$ ed, edited by Gennaro, 2000, pp. 246-256.

Rigo et al., "Growth, Weight Gain Composition and Mineral Accretion in Term Infants Fed a New Experimental Formula Containing Hydrolysed Protein, Beta-Palmitate and Prebiotics," *Pediatrika, Alpe*, Madrid, Spain, vol. 21, No. 10, 2001, pp. 387-396.

Roberfroid, et al, "The Bifidogenic Nature of Chicory Inulin and its Hydrolysis Products," *The Journal of Nutrition*, vol. 128, 1998, pp. 11-19.

Roberfroid, "Prebiotics: preferential substrates for specific germs?," *Am J. Clin. Nutr.*, vol. 73 (suppl), 2001, pp. 406S-409S.

Schmelzle et al, "Randomized Double-Blind Study of the Nutritional Efficacy and Bifidogenicity of a New Infant Formula Containing Partially Hydrolyzed Protein, a High β-Palmitic Acid Level, and Nondigestible Oligosaccharides," *J. Pediatr. Gastroenterol. Nutr.*, vol. 36, issue 3, Mar. 2003, pp. 343-351.

Simopoulos et al., "Workshop on the Essentiality of and Recommended Dietary Intakes for Omega-6 and Omega-3 Fatty Acids," *Journal of the American College of Nutrition*, vol. 18, No. 5, 1999, pp. 487-489.

Van Laere et al., "Mogelijkheden en toepassingen van prebiotica: Possibilities and applications of prebiotics," *Voedingsmiddelen Technologie*, Noordervliet B.V. Zeist, NL, vol. 34, No. 23, Oct. 26, 2001, pp. 51-54 (XP008029566; ISSN: 0042-7934).

Watanabe et al., "Therapeutic Effects of Glycyrrhizin in Mice Infected with LP-BM5 Murine Retrovirus and Mechanisms Involved in the Prevention of Disease Progression," *Biotherapy*, vol. 9, No. 4, 1996, pp. 209-220, Kluwer Academic Publishers, Dordrecht, NL.

WordNet Search 3.0 "prevent"; also available at http://wordnetweb.princeton.edu/perl/webwn; last viewed Mar. 16, 2010.

Bernhart, et al, "Lactulose in Modified Milk Products for Infant Nutrition," *J. Dairy Sci.*, 1956, pp. 399-400.

Bouhnik, et al., "Administration of Transgalacto-Oligosaccharides Increases Fecal Bifiobacteria and Modifies Colonic Fermentation Metabolism in Healthy Humans", American Society for Nutritional Sciences, pp. 444-448, 1997.

Cho, et al., "Complex Carbohydrates in Foods", Marcel Dekker Inc., N.Y., 1999.

Craig, et al., "Polydextrose as Soluble Fiber: Physiological and Analytical Aspects," 1998, pp. 370-376.

Crittenden, et al., "Production, properties and applications of food-grade oligosaccharides", Trends in Food Science & Technologies, vol. 7, Nov. 1996, pp. 353-361.

Cummings, J. H., "Gastrointestinal Effects of Food Carbodhydrate 1-3", Am J Clin Nutr, Apr. 1995; Suppl. 4 61 (suppl): pp. 938-945.

Detry, A., Dissertation 1992, Institut Paul Lambin "Implications technologiques et nutritionelles . . . ".

Dombo, et al., "Production Health Benefits and Applications of Galacto-oligosaccharides," Yalpani M. ed., *New Technologies for Healthy Foods and Neutraceuticals*, ATL Press, Shewsbury, MA, 1997, pp. 143-156.

Frisomum, Analysis Chart and Brochure, 1998.

Gibson et al., "Bifidogenic properties of different types of fructo-oligosaccharides", Food Microbiology, 1994, 11, pp. 491-498.

Gibson, et al., "Dietary Modulation of the Human Colonic Microbiota: Introducing the Concept of Prebiotics", American Institute of Nutrition, pp. 1401-1412, 1995.

Gibson, et al., "Dietary Modulation of the Human Colonic Mlcrobiota: Introducing the Concept of Prebiotics", American Institute of Nutrition, 0022-3166/1995, pp. 1401-1412.

Gibson, et al., "Selective stimulation of bifidobacteria in the Human Colon by Oligofructose and Inulin", Gastroenterology 1995, 108, pp. 975-982.

Haastrecht, "Oligosaccharides: Promising Performers in New Product Development," *IFI*, No. 1, 1995, pp. 23-27.

Hartemink, R., "Non-digestible oligosaccharides: healthy food for the colon?" Wageningen, The Netherlands, 1997, p. 130-131.

Hertzler, et al., "Colonic Adaptation to Daily Lactose Feeding in Lactose-Maldigesters Reduces Lactose-Intolerance," *Am. J. Clin. Nutr.*, 1996, pp. 232-236.

Ito, et al., "Effects of Administration of Galactooligosaccharides on the Human Faecal Microflora, Stool Weight and Abdominal Sensation", Microbial ecology in health and disease, vol. 3, pp. 285-292, 1990.

Ito, et al., "Effects of Transgalactosylated Disaccharides on the Human Intestinal Microflora nd Their Metabolism", J. Nutr. Sci. Vltaminol., 39, 279-288, 1993.

Ito, et al., "Influence of Galactooligosaccharides on the Human Fecal Microflora", J. Nutr. Sci. Vltaminol., 39, 635-640, 1993.

Ito, et al., "Influence of Lactose on Faecal Microflora in Lactose Maldigestors," *Microbial Ecology in Health and Disease*, vol. 6, 1993, pp. 73-76.

Jiang, et al., "In Vitro Lactose Fermentation by Human Colonic Bacteria is Modified by *Lactobacillus acidophilus* Supplementation," *American Society for Nutritional Sciences*, 1997, pp. 1489-1495.

Kohmoto, et al., "Effect of Isomalto-oligosaccharides on Human Fecal Flora", Bifidobacteria Microflora, vol. 7(2), pp. 61-69, 1988.

Listing of sales of RAFTIMIX®10 to clients La. iin period Sep. 13, 1996 to May 19, 1998.

Manufacture protocol with composition of RAFTIMIX®10 1995.

Mitsuoka, "Intestinal Flora and Human Health," *Asa Pacific J. Clin. Nutr.*, vol. 15, 1996, pp. 2-8.

Mizota, et al., "Lactulose as a Sugar with Physiological Significance," *Bulletin IDF*, No. 212, Trends in Whey Utilization, 1987, Chapter 11.

RAFTILINE HP Product Sheet, May 1995.
RAFTILINE®HP Product Sheet Release: May 1995.
RAFTILINE®ST Product Sheet Release: May 1995.
RAFTILOSSE®P95 Product Sheet Release: May 1995.
RAFTIMIX®10 Product Sheet Release: May 1995.

Roberfroid, et al., "Health Benefits of Non-Digestible Oligosaccharides," 1997.

Roberfroid, M., "Dietary Fiber, Inulin, and Oligofructose: a review comparing their physiological effects", Critical Reviews in Food Science and Nutricion, 33(2): 103-148, 1993.

Rotimi, et al, "The Development of the Bacterial Flora in Normal Neonates," 1981, pp. 51-61.

Rubaltelli, et al., "Intestinal Flora in Breast- and Bottle-fed Infants," 1998, pp. 186-190.

Salimen, et al., "Functional food science and gastrointestinal physiology and function", British Journal of Nutrition, 1998, 80, Suppl. 1, S147-S171.

Tanaka, et al., "Effects of Administration of TOS and Bifodobacterium breve 4006 on the Human fecal flora", Bifidobacteria Microflora, vol. 2(1), 17-24, 1983.

Terada, et al., "Effect of Lactosucrose on Fecal Flora and Fecal Putrefactive Products of Cats," 1993.

Van Loo, et al., "On the Presence of Inulin and Oligofructose as Natural Ingredients in the Western Diet," *Critical Reviews in Food Science and Nutrition*, vol. 35, No. 6, 1995, pp. 525-552.

Yazawa, et al., "Search for Sugar Sources for Selective Increase of Bifidobacteria", Bifdobacteria Microflora, vol. 1(1), pp. 39-44, 1982.

Fox, "Bovine Colostrum as a Resource for the Powerful Antioxicant Glutathione," Immune-Tree South Africa, Nov. 2008, pp. 1-7.

Igoe et al., Dictionary of Food Ingredients, 3rd Ed., Chapman and Hall, 1996, pp. 46, 66, 67, and 94.

Jirapinyo et al., "HIV Disease: Working Group Report of the First World Congress of Pediatric Gastroenterology, Hepatology, and Nutrition," J. Ped. Gastroenterology and Nutrition, vol. 35, Aug. 2002, pp. S134-S142.

Plettenberg et al., "A preparation from bovine colostrum in the treatment of HIV-positive patients with chronic diarrhea," Clinical Investigator, vol. 71, 1993, pp. 42-45.

Guggenbichler et al., "Acidic oligosaccharides from natural sources block adherence of *Escherichia coli* on uroepithelial cells," Pharm. Pharmacol. Lett., vol. 7, No. 1, Jun. 1997, pp. 35-38.

Roman et al., "Original Communication Nutritional treatment for acquired immunodeficiency virus infection using an enterotropic peptide-based formula enriched with n-3 fatty acids: a randomized prospective trial," European Journal of Clinical Nutrition, vol. 55, 2001, pp. 1048-1052.

Agostoni et al., "From nutrient composition to infants' function," Minerva Pediatrica, vol. 55, No. 3, 2003, pp. 181-194.

Alles et al., "Current trends in the composition of infant milk formulas," Current Paediatrics, vol. 14, 2004, pp. 51-63.

Barcelo et al., "Mucin secretion is modulated by luminal factors in the isolated vascularly perfused rat colon," Gut, vol. 46, 2000, pp. 218-224.

Campbell et al., "An Enteral Formula Containing Fish Oil, Indigestible Oligosaccharides, Gum Arabic and Antioxidants Affects Plasma and Colonic Phospholipid Fatty Acid and Prostaglandin Profiles in Pigs," Journal of Nutrition, vol. 127, No. 1, Jan. 1997, pp. 137-145.

Caplan et al., "Effect of Polyunsaturated Fatty Acid (PUFA) Supplementation on Intestinal Inflammation and Necrotizing Enterocolitis (NEC) in a Neonatal Rat Model," Pediatric Research, vol. 49, No. 5, 2001, pp. 647-652.

Carlson et al., "Lower Incidence of Necrotizing Enterocolitis in Infants Fed a Preterm Formula with Egg Phospholipds," Pediatric Research, vol. 44, issue 4, Oct. 1998, pp. 491-498.

Carver et al., "The role of nucleotides in human nutrition," J. Nutr. Biochem., vol. 6, Feb. 1995, pp. 58-72.

Claud et al., "Hypothesis: inappropriate colonization of the premature intestine can cause neonatal necrotizing enterocolitis," The FASEB Journal, vol. 15, Jun. 2001, pp. 1398-1403.

Connor et al., "Increased Docosahexaenoic Acid Levels in Human Newborn Infants by Administration of Sardines and Fish Oil During Pregnancy," Lipids, vol. 31, Supplement, 1996, pp. S-183-S-187.

FAO Corporate Document, "The relationship between food composition and available energy," Provisional Agenda Item 4.1.3, Oct. 5-17, 1981, Rome, by D.A.T. Southgage, A.R.C. Food Research Institute, Norwich, UK, 10 pages.

Kirk-Othmer, Encyclopedia of Chemical Technology, 4th Ed., vol. 12, 1994, pp. 855-856.

Kleessen et al., "Fructans in the diet cause alterations of intestinal mucosal architecture, released mucins and mucosa-associated bifidobacteria in gnotobiotic rats," British Journal of Nutrition, vol. 89, 2003, pp. 597-606.

Koletzko et al., "Growth, development and differentiation: a functional food science approach," British Journal of Nutrition, vol. 80, Suppl. 1, 1998, pp. S5-S45.

Martin-Sosa et al., "Sialyloligosaccharides in Human and Bovine Milk and in Infant Formulas: Variations with the Progression of Lactation," J. Dairy Sci., vol, 86, 2003, pp. 52-59.

Meslin et al., "Effects of galacto-oligosaccharide and bacterial status on mucin distribution in nucosa and on large intesitne fermentation in rats," British Journal of Nutrition, vol. 69, 1993, pp. 903-912.

ProBLEN Anti-Aging Supplements, "Digestive Enzyme with Probiotics," Brochure dated Aug. 20, 2010, 4 pages.

Stockman et al., "Mechanisms of Epithelial Barrier Impairment in HIV Infection," Annals New York Academy of Sciences, 2000 pp. 293-303.

Szilagyi, "Review article: lactose—a potential prebiotic," Ailment Pharmacol Ther, vol. 16, 2002, pp. 1591-1602.

Willemsen et al., "Short chain fatty acids stimulate epithelial mucin 2 expression through differential effects on prostaglandin E1 and E2 production by intestinal myofibroblasts," www.gutinl.com, 2003, pp. 1442-1447.

Marteau et al., "Nutritional advantages of probiotics and prebiotics," *British Journal of Nutrition*, vol. 87, Sup. 2, 2002, pp. S153-S157.

MayoClinic.com, "Ulcerative colitis," also available at http://www/mayoclinic.com/health/ulcerative-colitis/DS00598/METHOD=print&DSECT . . . , last viewed Nov. 24, 2010.

Reddy et al., "Effect of dietary oligofructose and inulin on colonic preneoplastic aberrant crypt foci inhibition," *Carcinogenesis*, vol. 18, No. 7, 1997, pp. 1371-1374.

* cited by examiner

CARBOHYDRATES MIXTURE

CROSS-REFERENCE TO RELATED APPLICATIONS

This application is a continuation of U.S. application Ser. No. 11/649,879, filed Jan. 5, 2007, which is a continuation of U.S. application Ser. No. 09/774,188, filed Mar. 20, 2001, which is a National Stage of PCT/EP99/05878, filed Aug. 11, 1999; the entire disclosures of which are incorporated herein by reference.

The invention relates to carbohydrate mixtures for dietetic foods and pharmaceuticals, dietetic and pharmaceutical compositions containing said carbohydrate mixtures, and to the use of said carbohydrate mixtures for stimulating the human large intestinal flora.

As is generally known, carbohydrates represent one of the essential foundations of nutrition. This is the reason why the most differing carbohydrates are admixed to the most differing foods and also to pharmaceuticals. The task of the carbohydrates therefore is primarily of the nutritive kind, and they serve as roughage respectively.

Carbohydrates consist of monosaccharides, and are respectively composed thereof. Depending on their polymerization degree, the carbohydrates are indicated as oligosaccharides or polysaccharides or glycans respectively. The carbohydrates thereby are present as free oligosaccharides, as well as in a bonded form such as for example in glycoproteins, proteoglycans and glycolipids.

Due to the variability of the monomers forming the carbohydrates, and due to the position of the glycosidic bond and the anomeric state of the carbohydrates and their conjugates, said carbohydrates and their conjugates represent an extremely heterogeneous and extensive substance class.

Carbohydrates have most differing biological functions. Thus, they influence, for example, the bacterial colonization of the large intestine, which is a prerequisite for its normal function. The microflora of the large intestine takes part in the intestinal functions in a very complex manner. This influence is preponderantly exercised by the fermentation of food components, which have not been resorbed in the small intestine. The fermentation encompasses a plurality of functions such as the further digestion of these food components, the detoxification of endogenously occurring metabolites, the synthesis of new metabolites, some of them having a very specific effect, the return resorption of bile acids, and many other processes. The normal microflora also has a health-promoting effect in that it suppresses the growth of other pathogenous microorganisms.

Bacteria, which produce lactic acid as their most important final metabolite (so-called lactic acid-producing bacteria), play an essential role as the important representatives of the normal microflora of the large intestine. Examples for this group are bacteria of the *lactobacillus* and *bifidobacterium* genus. Therefore, efforts have been undertaken for an extended period of time on ways to control the development of a lactic acid-dominant intestinal flora by means of dietetic measures. This is particularly important in cases when a normal intestinal flora is not present or not sufficiently present due to processes caused by the development such as, for example, of new born babies or due to pathogenous states such as, for example, subsequent to an enteral antibiotic therapy or another drug therapy or during and after enteral infections.

Carbohydrates are now increasingly used in food, "functional food" and pharmaceuticals under the aspect of a biological efficiency. Thus, it is, for example, known that some carbohydrates exercise a growth-promoting effect upon various species of *bifidobacteria*, but also upon lactobacilli. Thus, galacto oligosaccharides, for example, have a growth-promoting effect upon *lactobacillus casei*. To date, however, only very specific species of carbohydrates having determined properties are used for promoting certain biological actions.

Thus, WO 98/26787, for example, describes the use of β-glucan and compounds derived thereof for the promotion of the population of lactic acid-producing microorganisms in the gastrointestinal tracts of human beings and animals. Mixtures may also be used, which contain further prebiotic substances, the latter not being specified in detail.

Moreover, mixtures are known from WO 96/13271, which contain various oligosaccharides and polysaccharides apart from immunoglobulins. These mixtures are used as a dietetic supplement, which, with oral administration, is supposed to be active against various gastrointestinal pathogens. The saccharides used are thereby indicated as soluble dietetic fibre, whereby it concerns inulin, fructo-oligosaccharides, pectin, guar gum and mixtures thereof.

In EP 0 756 828 A1, fibre-containing nutrient compositions are described, which contain in addition to oligosaccharides and/or starch, soluble polysacchararides not representing starch and insoluble polysaccharides not representing starch.

It is the object of the present invention to provide improved carbohydrate mixtures, which may be incorporated in dietetic nutritions and pharmaceuticals, and which, in addition to their nutritive effect, also stimulate health-promoting microorganisms present in the natural flora of the large intestine.

This object is solved by means of carbohydrate mixtures according to the teaching of the present claims.

Thus, the carbohydrate mixtures according to the present invention, contain at least two different, essentially soluble carbohydrate components A and B, which remain undigested in the gastrointestinal tract and reach the large intestine unresorbed. The carbohydrate mixtures according to the present invention may also consist exclusively of these two carbohydrate components A and B.

Carbohydrate component A thereby consists of at least one monosaccharide or from at least one oligosaccharide. Oligosaccharides are thereby understood as those comprising of 2 to 7 monosaccharide units. Hence, the oligosaccharides refer to disaccharides, trisaccharides, tetrasaccharides, pentasaccharides and hexaasaccharides. Carbohydrate component A may also be formed by a compound of two or more of the mentioned saccharides. It may therefore be comprised of only one monosaccharide or of a mixture of two or more monosaccharides or of a mixture of one or more monosaccharide/s with one or more oligosaccharide/s. It may also be comprised of any arbitrary number of various monosaccharides and/or oligosaccharides of that kind.

Carbohydrate component B consists of at least one polysaccharide comprising 7 or more monosaccharide units. Polysaccharides are understood as those starting from heptasaccharide (e.g. heptasaccharide, oktasaccharide, nonasaccharide, decasaccharid, etc.). Carbohydrate component B, may also be comprised of only one polysaccharide of that kind or of any arbitrary number of polysaccharides of that kind.

Accordingly, when in the following or in the claims, a carbohydrate component A or B is mentioned, it may refer to any one of all of these variants.

Carbohydrate component A thereby represents up to 95 wt-% of the sum of carbohydrate component A and carbohydrate component B (A+B=100 wt-%). Carbohydrate component B represents 5 to 95 wt-% of the sum of carbohydrate component A and carbohydrate component B.

At least 80 wt-% of the carbohydrates or saccharides out of the sum of carbohydrate component A and B thereby have a prebiotic effect. Preferably, at least 80 wt-% of the carbohydrates belonging to carbohydrate component A, and also at least 80 wt-% of those belonging to carbohydrate component B, have a prebiotic effect. In other words, preferably at least 80 wt-% each of the carbohydrates or saccharides out of carbohydrate components A and B, are intended to reach the large intestine in an undigested (hence not resorbable in the small intestine) manner. In other words, these carbohydrates or saccharides of carbohydrate components A and B in the gastrointestinal tract are neither resorbed and digested in the stomach nor in the small intestine, but reach the large intestine as such.

The proportion of the not prebiotically active carbohydrates or saccharides of carbohydrate components A and B therewith amounts to a maximum of 20 wt-%. These carbohydrates or saccharides refer to those, which are actually soluble, but can be excreted in an undigested form. These carbohydrates can exercise a physical effect in that they increase, for example, the volume of the faeces or prompt a water adsorption.

Soluble carbohydrates in the sense of the present invention are understood as those, which form a homogenous solution in the physical sense in water, in a concentration of at least 1 g/l at room temperature (e.g. pursuant to Roempp's Chemie Lexikon).

Such as it has already been stated, the inventive carbohydrate mixtures may consist exclusively of the carbohydrate components A and B or may contain them. For the assessment of the proportion determining the carbohydrate components A and B in a dietary or pharmaceutical product, the following steps are carried out:

In a first stage, all soluble carbohydrates are extracted from the product by means of water. Fats and proteins are removed from the extract.

In a second stage, the soluble carbohydrates, or the extract respectively, are digested by means of human enzymes, e.g. human amylase, human pancreatic juice or a small intestine ciliated border preparations. The thereby resulting non-digested carbohydrates (except for the in-vivo-resorbable monosaccharides obtained in this in-vitro experiment), constitute the two carbohydrate components A and B, and 80% thereof are supposed to be prebiotically active.

A prebiotically active carbohydrate according to the present invention is understood as a carbohydrate, which reaches the large intestine undigested (and hence is not resorbable in the small intestine), and there, it selectively encourages the growth and/or the activity of one or of a restricted number of bacterial species in the intestine, and consequently promotes health. This prebiotic effect of such carbohydrates and their specific mechanisms are described in detail in "G. R. Gibson & M. B. Roberfroid, *J. Nutr.* 1995; 125: 1401-1412", whereto explicit reference is herewith made, and the disclosure of which is included in the present documents.

The inventive carbohydrate mixtures hence are those, wherein the carbohydrates, which are soluble and undigested in the sense described above, fulfil the herein specified criteria and constitute the carbohydrate components A and B.

Apart from these carbohydrate components A and B, other carbohydrates may be present as well. Amongst those are 1.) the actually soluble but digestible carbohydrates, which are digestible according to the above-described second stage, and 2.) the insoluble carbohydrates, which are resorbable./.digestible or even not resorbable./.digestible.

These carbohydrates enumerated sub 1.) and 2.), may be present as such in any arbitrary quantities in addition to the carbohydrate components A and B, in each case depending on the desired final product. Preferably, the insoluble carbohydrates constitute 0 to 10 wt-% of the carbohydrate mixtures.

Carbohydrate component A may, for example, consist of one or more of the following carbohydrates: β-galactooligosaccharides, α-galactooligosaccharides, fructo-oligosaccharides, fuco-oligosaccharides, manno-oligosaccharides, xylo-oligosaccharides, sialyl-oligosaccharides, N-glycoprotein oligosaccharides, O-glycoprotein oligosaccharides, glycolipid oligosaccharides, cello-oligosaccharides, chitosan-oligosaccharides, chitin-oligosaccharides, galacturono-oligosaccharides, glucurono-oligosaccharides, β-glucan oligosaccharides, arabinoxylo-oligosaccharides, arabinogalacto-oligosaccharides, xylogluco-oligosaccharides, galactomanno-oligosaccharides, rhamno-oligosaccharides.

Carbohydrate component B may, for example, be formed of one or more of the following carbohydrates or saccharides:

Soluble carbohydrates or saccharides: fruct(os)anes/inulins, galactans, fucoidans, arabinans, xylans, xanthans, β-glucans, galacturonans, N-glycans, O-glycans, hyaluronic acids, chondroitins, xyloglucans, arabinogalactans, alginates, carageenanes, galactomannans, arabinoxylanes, glycolipid glycans, glycoprotein glycans, proteoglycans.

By means of a selective combination of oligosaccharides and polysaccharides, and consequently the simultaneous presence of carbohydrate components A and B, the health-promoting microorganisms in the large intestine may be promoted by an essentially higher efficiency than it would be the case with only one of said carbohydrate components. Thus, it is possible with the administration of the inventive combination, to make very rapid restitution of a normal large intestinal flora, to maintain same or to prophylactically prevent an alteration of the intestinal flora during situations of stress, and thus to influence the bacterial colonization of the large intestine in a way, which is more efficient than the one with the previously used carbohydrates.

According to a preferred embodiment, at least 80 wt-% of carbohydrate component A as well as of carbohydrate component B consist of carbohydrates, which are bifidogenous and./.or which promote lactic acid bacteria. Due to such a combination of oligosaccharides and polysaccharides having said properties, the growth of the lactic acid bacteria may surprisingly be promoted in an essentially stronger manner than this would be the case with oligosaccharides or polysaccharides alone. Not only lactic acid bacteria are thereby promoted, which are naturally present in the intestine, but also the growth of those is promoted—optionally even in a selective manner—which are introduced exogenously.

Apart from this indirect action via the bacteria themselves and their metabolites such as fatty acids (butyrate, propionate, etc.), pH effects and stimulation of colonozytes, direct physical effects such as peristalsis, water content, quantity of faeces, mechanical action upon the intestinal mucosa are likewise positively influenced.

Thus, the inventive carbohydrate mixtures dispose not only of a nutritive effect but also of a wide spectrum of activities. In addition to the above-described biological effects, the following may also be achieved by means of the inventive mixtures: stabilization of a natural microflora, prevention of pathogenous substances./.organisms such as toxins, viruses, bacteria, fungi, transformed cells and parasites from adhering, dissolution of complexes of toxins, viruses, bacteria, fungi and other pathogens having endogenous cells, as well as their elimination from the body, and an acceleration of wound healing.

Thus, the inventive mixtures are suitable for the prophylaxis and/or the treatment of symptoms/diseases occurring in conjunction with a disturbed intestinal flora, for example, as a consequence of the association./.adhesion of the mentioned substances and organisms with/on epithelia or other endogenous cells.

The carbohydrates or saccharides of carbohydrate components A and B primarily differ in size. Nevertheless, mixtures have found to be particularly efficient, wherein the carbohydrates or the saccharides of carbohydrate component A, on the one hand, and of carbohydrate component B, on the other hand, are of a different structure. This different structure may, for example, concern the monosaccharide composition when, for example, fructans are used on the one hand, and galactans, on the other hand. This different structure may likewise concern the glycosidic bonding (e.g. α-galacto oligosaccharaides versus β-galacto oligosaccharaides or α-glucans (starch) versus β-glucans (cellulose)). The monomer composition, as well as the glycoside bonding may have an influence on the chemical behaviour (e.g. solubility) or on the physiological behaviour (e.g. digestibility).

The core of the inventive mixtures may inter alia be seen in that carbohydrates of different sizes are used, which preferably and additionally belong to at least two different "classes". With an administration of such mixtures, a synergetic effect may occur relative to the prebiotic effects of the separate substance groups A and B.

Thus, the carbohydrates of component A may not belong to one substance class alone but may also be formed out of several classes (for example A: galacto-oligosaccharides plus fuco-oligosaccharides), whereas the carbohydrates of component B may equally originate from one substance class and also from several substance classes (for example B: inulins plus xylans).

According to a further preferred embodiment, the carbohydrate component A constitutes 95 to 60 wt-%, and in particular about 90 wt-%, and the carbohydrate component B 5 to 40 wt-%, and in particular about 10 wt-% of the carbohydrates present in toto.

Particularly efficient mixtures are those wherein at least 60 wt-%, and in particular 80 to 100 wt-% of the carbohydrates of carbohydrate component A belong to the group of the galacto-oligosaccharides, and at least 60 wt-%, and in particular 80 to 100 wt-% of the carbohydrates of carbohydrate component B belong to the group of the fructo-polysaccharides. Galacto-oligosaccharides are composed of galactose residues of different glycosidic bonds, in particular at the β 1-4 and β 1-6 position. At the reducing end, at β 14 of a glycosidic bond, glucose can be present. Fructo-polysaccharides, fructans, inulins and levans being part thereof, are composed of fructose residues of glycosidic bonds at the β 2-1 and β-6 position. At the reducing end, at β 2-1 of a glycosidic bond, glucose can be present.

When a range is mentioned within the scope of the present invention, said range indication will encompass and disclose at least all integral intermediate values, and even all narrower ranges embraced by the wider range. This means that for carbohydate component A as well as for carbohydrate component B, which may both constitute 5 to 95 wt-%, that all intermediate values such as 6, 7, 8, 9 . . . 13, 14 . . . 25, 26, 27 . . . 30, 31, 32, 33 . . . 38, 39, 40, 41 . . . 47, 48, 49, 50, 51 . . . 59, 60, 61, 62, 63 . . . 72, 73, 74 . . . 79, 80, 81, 82 . . . 87, 88, 89, 90, 91, 92, 93 and 94 wt-% are likewise covered.

The same applies to the indication that at least 80 wt-% of the carbohydrates of carbohydrate component A and at least 80 wt-% of the carbohydrates of carbohydrate component B are prebiotically active or promote lactic acid bacteria and/or are bifidogenic. Thus, the term "at least 80 wt-%" designates at least all single values between 80 wt-% and 100 wt-%, and hence, for example, 81, 82, 83, 84, 85, 86, 87, 88, 89, 90, 91, 92, 93, 94, 95, 96, 97, 98, 99 and 100 wt-%. The carbohydrate components A and B may therewith exclusively consist of such carbohydrates.

The mixing ratio between carbohydrate component A and carbohydrate component B hence is 5 to 95 wt-%, or 95 to 5 wt-% respectively, and in particular 95 to 60, or 5 to 40 wt-% respectively. Thus, at least all integral narrower ranges are disclosed as well. The weight ratio between carbohydrate component A and carbohydrate component B may therefore, for example, be 50:50, 51:49, 52:48, 53:47, 54:46, 55:45, 56:44, 57:43, 58:42, 49:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, and 95:5.

The molecular weight of the polysaccharides may thereby be of some MDas, and may be extended to particular carbohydrates. Preferably, however, polysaccharide molecules are used comprising up to 100 monosaccharide units.

For the production of the inventive carbohydrate mixtures, carbohydrates and carbohydrate mixtures known to date und used in particular for the production of foods or food products can be used. It is also possible to use raw materials previously modified in a technical way. The preparation of the inventive mixtures may thereby ensue by means of a simple blending of the correspondingly selected carbohydrates or oligosaccharides with polysaccharides or the carbohydrate mixtures. The initial components must thereby be so mixed with one another that the inventive parameters are respected with the finished inventive mixtures.

As raw materials may be used reserve carbohydrates (fructans, galacto-oligosaccharides from legumes, fucoidan, α-glucane, laminarin, carragenan, mannans, galactomannans, agar), natural gum, N-glycosidic bonded carbohydrates of glycoproteins, O-glycosidic bonded carbohydrates of glycoproteins, glycans of glycolipids, enzymaticly prepared carbohydrates (galacto-oligosaccharides, gluco-oligosaccharides, xylo-oligosaccharides), bacterial carbohydrates (such as xanthans), as well as oligosaccharides (galacto-oligosaccharides, gluco-oligosaccharides (from α 1-2 and α 1-3 glucose residues), xylo-oligosaccharides), as well as skeletal carbohydrates such as celluloses, hemicelluloses (arabinans, galactans), pectins and chitins may be used. The substances should preferably be of food-grade (cf. Complex Carbohydrates in Foods, British Nutrition Foundation; Chapman & Hall, London 1990). It is also possible to carrying out an enzymatic modification of the raw materials by means of hydrolases (e.g. glycosidases, transglycosidases and lipases), transferases, isomerases (e.g. aldolases and ketolases), oxidoreductases (e.g. oxidases) and reductases (e.g. glucosedehydrogenases), lyases (e.g. polysaccharide lyases) and ligases of the raw materials and products. Moreover, it is possible to carry out a technical modification of the raw materials and products, namely by means of pressure (e.g. extrusion), temperature (e.g. caramelization), organic syntheses, organic modification (e.g. carboxymethylation and per-acetylation), acid and/or alkaline hydrolysis and fractionation (e.g. depending on size and/or physico-chemical parameters such as charge and hydrophobicity).

The inventive carbohydrate mixtures thereby are essentially composed of the hereinafter listed monosaccharides and of the thereof composed oligosaccharides and polysaccharides: D-glucose, D-fructose, D-galactose, D-mannose, L-fucose, D-N-acetylglucosamine, D-N-acetylgalactosamine, D-xylose, L-rhamnose, D-arabinose, D-allose, D-talose, L-idose, D-ribose, as well as monosaccharides comprising carboxyl groups such as D-galacturon acid, D-glucuron acid, D-mannuron acid and/or the methylated forms thereof such as N-acetylneuramin acid, N-glycolylneuramin acid and/or the O-acetylated forms thereof.

Moreover, these monomers and the thereupon based higher units can be modified by means of —$OSO_3H$ groups and/or —$OPO_3H$ groups.

The subject matter of the present invention is also dietetic or pharmaceutical compositions containing said inventive carbohydrate mixtures, and the use of said above-described carbohydrate mixtures for promoting the flora of the large intestine in humans. The term "promoting/promotion" represents a general term for all of the above-listed biological actions. Thereto belongs in particular the promotion of the growth of lactic acid-producing bacteria.

The inventive mixtures may be present in the following products:

Formulas for prematurely born babies, formulas for maturely born babies, infant formulas, human milk fortifier, clinical nutrition (in general, the inventive mixture may replace a part or the entirety of other components in these nutritions, such as, for example, lactose, maltodextrin or starch, or may be added to the nutrition), pharmaceuticals, dietetic supplement (as sachet in drinks).

In the following, carbohydrate mixtures representing various preferred embodiments are described. The indications thereby refer to weight percent, if not indicated otherwise. In these examples it is stated to which carbohydrate components A or B the used carbohydrates belong. The carbohydrate component A is thereby only called "A", and carbohydrate component B only "B".

EXAMPLE 1

Composition
90% A=galacto-oligosaccharides
transgalacto-oligosaccharides, e.g. Elixor® (Company Borculo, enzymatic from lactose by means of β-galactosidase)
10% B=inulin
Inulin, e.g. Raftiline® HP (Company Orafti, extraction from chicories, physical separation of the low-molecular oligosaccharides)

For the preparation of the transgalacto-oligosaccharides (Elixor®), lactose is treated with β-galactosidase. The lactose is thereby catalytically transformed in galacto-oligosaccharides, whereby a plurality of galacto-oligosaccharides are formed having varying chain lengths. Primarily, disaccharides and trisaccharides comprising 3 or 2 galactose units are thereby obtained.

EXAMPLE 2

Composition
60% A=galacto-oligosaccharides
transgalacto-oligosaccharides (enzymatic from lactose by means of β-galactosidase)
40% B=inulin
Inulin, e.g. Raftiline® HP (Company Orafti, extraction from chicories, physical separation of the low-molecular oligosaccharides)

EXAMPLE 3

Composition
90% A=galacturon acid oligosaccharides
enzymatic from pectin
10% B=xylose polysaccharides
enzymatic from xylan (vegetable hemicellulose)

EXAMPLE 4

Composition
90% A=fructo-oligosaccharides
enzymatic from inulin by means of endo-inulinase
10% B=cellulose polysaccharides
enzymatic from cellulose by means of cellulase

EXAMPLE 5

Composition
90% A=galacto-oligosaccharides
10% B=arabinans
enzymatic from vegetable hemicellulose

EXAMPLE 6

Composition
55% A=galacto-oligosaccharides
45% B=fructo-polysaccharides

EXAMPLE 7

Composition
85% A=galacturon acid oligosaccharides
15% B=fructo-polysaccharides

EXAMPLE 8

Composition
90% A=gluco-oligosaccharides
enzymatic by means of glucosyltransferase
10% B=fructo-polysaccharides

EXAMPLE 9

Composition
90% A=fuco-oligosaccharides
enzymatic from algae fucoidan
10% B=fructo-polysaccharides

EXAMPLE 10

Composition
90% A=galacto-oligosaccharides
10% B=fuco-polysaccharides
enzymatic from algae fucoidan

EXAMPLE 11

Composition
55% A=galacto-oligosaccharides
α-galacto-oligosaccharides from soya
45% B=fucto-polysaccharides (inulin)

EXAMPLE 12

Composition
80% A=transgalacto-oligosaccharaides
10% A=galacturon acid oligosaccharides
10% B=inulin What claimed is:

1. A dietetic or pharmaceutical composition comprising at least two soluble carbohydrate components A and B, which components remain undigested in the gastrointestinal tract and enter the large intestine without being resorbed,
   carbohydrate component A comprising oligosaccharides having 2 to 6 monosaccharide units, 80 to 100 weight percent of which oligosaccharides comprise galacto-oligosaccharides,
   carbohydrate component B comprising polysaccharides having 7 or more monosaccharide units, 80 to 100 weight percent of which polysaccharides comprise fructo-polysaccharides, and
   carbohydrate component A and carbohydrate component B being present in a weight ratio of about 9 to about 1, respectively.

2. The composition of claim 1, which comprises a dietetic food.

3. The composition of claim 2, in which the dietetic food is selected from the group consisting of formulas for prematurely born babies, formulas for maturely born babies, infant formulas, human milk fortifier, clinical nutrition products or portions thereof, and dietetic supplements.

4. The composition of claim 2, in which the dietetic food is an infant formula.

5. The composition of claim 2, which comprises a pharmaceutical product.

6. The composition of claim 1, further comprising digestible carbohydrates, insoluble carbohydrates or mixtures thereof.

7. The composition of claim 1, further comprising xanthans, gluco-oligosaccharides, xylo-oligosaccharides, or mixtures thereof.

8. The composition of claim 1, in which carbohydrate component B comprises polysaccharides having 7 to 100 monosaccharide units.

9. An infant formula comprising at least two soluble carbohydrate components A and B, which components remain undigested in the gastrointestinal tract and enter the large intestine without being resorbed, carbohydrate component A comprising oligosaccharides having 2 to 6 monosaccharide units, 80 to 100 weight percent of which oligosaccharides comprise galacto-oligosaccharides,
   carbohydrate component B comprising polysaccharides having 7 or more monosaccharide units, 80 to 100 weight percent of which polysaccharides comprise fructo-polysaccharides, and
   protein, fat, insoluble carbohydrate, digestible carbohydrate, or combinations thereof,
   wherein carbohydrate component A and carbohydrate component B are present in a weight ratio of about 9 to about 1, respectively.

10. A method of preparing a dietetic or pharmaceutical composition comprising:
    (a) selecting a carbohydrate component A comprising oligosaccharides having 2 to 6 monosaccharide units, 80 to 100 weight percent of which oligosaccharides comprise galacto-oligosaccharides,
    (b) selecting a carbohydrate component B comprising polysaccharides having 7 or more monosaccharide units, 80 to 100 weight percent of which polysaccharides comprise fructo-polysaccharides,
    (c) optionally selecting one or more an additional components for the dietetic or pharmaceutical composition, and
    (d) combining carbohydrate component A, carbohydrate component B and, optionally, the one or more additional components, such that carbohydrate component A and carbohydrate component B are present in a weight ratio of about 9 to about 1, respectively.

11. The method of claim 10, in which the composition comprises a dietetic food.

12. The method of claim 11, in which the dietetic food is selected from the group consisting of formulas for prematurely born babies, formulas for maturely born babies, infant formulas, human milk fortifier, clinical nutrition products or portions thereof, and dietetic supplements.

13. The method of claim 10, in which the additional component comprises digestible carbohydrates, insoluble carbohydrates, or mixtures thereof.

14. The method of claim 10, in which the additional component comprises xanthans, gluco-oligosaccharides, xylo-oligosaccharides, or mixtures thereof.

15. The method of claim 10, in which carbohydrate component B comprises polysaccharides having 7 to 100 monosaccharide units.

16. An infant formula composition comprising:
    (a) soluble, indigestible oligosaccharides having 2 to 6 monosaccharide units, 80 to 100 weight percent of which oligosaccharides comprise galacto-oligosaccharides, and
    (b) soluble, indigestible polysaccharides having 7 or more monosaccharide units, 80 to 100 weight percent of which polysaccharides comprise fructo-polysaccharides, and wherein the oligosaccharides and polysaccharides are present in a weight ratio of about 9 to about 1, respectively.

* * * * *